United States Patent

Marion et al.

(10) Patent No.: US 9,267,015 B2
(45) Date of Patent: Feb. 23, 2016

(54) SOLVENT MEDIA COMPRISING BRANCHED CARBOXYLIC ACID DIESTERS

(75) Inventors: Philippe Marion, Vernaison (FR); Lise Trouillet-Fonti, Lyons (FR); Jean-Marie Bernard, Saint-Laurent d'Agny (FR)

(73) Assignee: RHODIA OPERATIONS, Aubervilliers (FR)

( * ) Notice: Subject to any disclaimer, the term of this patent is extended or adjusted under 35 U.S.C. 154(b) by 317 days.

(21) Appl. No.: 12/281,793

(22) PCT Filed: Mar. 2, 2007

(86) PCT No.: PCT/FR2007/000370
§ 371 (c)(1),
(2), (4) Date: Feb. 6, 2009

(87) PCT Pub. No.: WO2007/101929
PCT Pub. Date: Sep. 13, 2007

(65) Prior Publication Data
US 2009/0224204 A1   Sep. 10, 2009

(30) Foreign Application Priority Data
Mar. 7, 2006  (FR) .................... 06 02011

(51) Int. Cl.
*B01F 1/00* (2006.01)
*C08K 5/11* (2006.01)
*C07C 67/22* (2006.01)

(52) U.S. Cl.
CPC . *C08K 5/11* (2013.01); *C07C 67/22* (2013.01); *C08K 2201/014* (2013.01)

(58) Field of Classification Search
USPC .......... 560/204, 191, 145, 211; 562/517, 522, 562/497, 564, 462, 591, 125.3; 252/364
See application file for complete search history.

(56) References Cited

U.S. PATENT DOCUMENTS

| 2,801,263 | A | * | 7/1957 | Hasek et al. ............... 560/204 |
| 3,567,749 | A | * | 3/1971 | Neubebauer et al. ........... 560/84 |
| 4,999,453 | A | * | 3/1991 | Merger et al. ............... 560/211 |
| 7,399,883 | B2 | * | 7/2008 | Brunel et al. ............... 562/550 |

FOREIGN PATENT DOCUMENTS

| DE | 2 950 100 A1 | 6/1981 |
| EP | 0 055 875 A1 | 7/1982 |

OTHER PUBLICATIONS

Matsuda, The cobalt Carbonyl-catalyzed Hydroesterification of Butadiene with carbon monoxide and methanol, 1973, Bulletin of the chemical society of japan, vol. 46 524-530.*
Matsuda, "The Cobalt Carbonyl-catalyzed Hydroesterification of Butadiene with Carbon Monoxide and Methanol" *Bulletin of the Chemical Society of JP* 1973 vol. 46 No. 2 pp. 524-530 XP002407465.
Marketta, "Liquid-Liquid Equilibria of Selected Dibasic Ester + Water + Solvent Ternary Systems" *Journal of Chemical and Engineering Data, American Chemical Society US* 1996 vol. 41 pp. 235-238 XP002407466.
International Search Report PCT/FR2007/000370 dated Jul. 26, 2007.

* cited by examiner

*Primary Examiner* — Monique Peets
(74) *Attorney, Agent, or Firm* — Dentons US LLP

(57) ABSTRACT

Compositions containing particular branched carboxylic acid diesters obtained from a mixture of branched dinitriles exhibit especially advantageous solvating properties and thus are useful substitutes for conventional solvents, in particular halogenated solvents.

7 Claims, No Drawings

SOLVENT MEDIA COMPRISING BRANCHED CARBOXYLIC ACID DIESTERS

CROSS-REFERENCE TO PRIORITY/PCT APPLICATIONS

This application claims priority under 35 U.S.C. §119 of FR 0602011, filed Mar. 7, 2006, and is a continuation/national phase of PCT/FR 2007/000370, filed Mar. 2, 2007 and designating the United States (published in the French language on Sep. 13, 2007, as WO 2007/101929 A1; the title and abstract were also published in English), each hereby expressly incorporated by reference in its entirety and each assigned to the assignee hereof.

The present invention relates to carboxylic acid diesters exhibiting in particular advantageous solvating properties which can be used as a substitute for conventional solvents, in particular halogenated solvents.

The invention relates more particularly to a composition formed of branched carboxylic acid diesters which are obtained from a mixture of dinitriles. This mixture of dinitriles is obtained as distillation fraction during the recovery and purification of adiponitrile in the process for the manufacture of the latter compound by double hydrocyanation of butadiene.

An oxygenated solvent has been provided for several years. This solvent is based on diesters obtained by esterification of a mixture of dicarboxylic acids, more particularly of a mixture of adipic acid, glutaric acid and succinic acid. This mixture of acids is obtained in the process for the manufacture of adipic acid by oxidation of cyclohexanol and/or cyclohexanone.

This solvent, for example sold by Rhodia under the trade name Rhodiasolv RPDE or by Invista under the trade name DBE, is used in numerous applications, in particular as a replacement for hydrocarbon solvents, chlorinated solvents or oxygenated solvents (glycol ethers, acetone).

In addition to this technical performance, which is a result of its solvating power and of its physicochemical properties, this oxygenated solvent exhibits the advantage of being less damaging to the environment, of being biodegradable and of being easy to recycle. Its highly favourable toxicological profile makes it possible to eliminate any risk to the final user. In addition, the physicochemical properties, such as the low volatility and the flash point, allow it to be used in complete safety.

It can also be used as a mixture with other solvents, such as N-methylpyrrolidone (NMP), without affecting the solvent properties but while reducing the cost of this.

Furthermore, this solvent is stable at ambient temperature and exhibits a low vapour pressure.

Oxygenated solvents exhibiting good solvating properties and without risk of toxicity and without danger to the environment are experiencing very strong growth. It is therefore important for the industrial sector to find and provide novel solvents exhibiting properties at least similar or equivalent to those of the solvents already available, such as the abovementioned RPDE.

One of the aims of the present invention is to provide a novel oxygenated solvent exhibiting physical properties, solvent properties, a toxicological profile and an ecotoxic impact which are similar or improved with respect to the solvent based on diesters of a mixture of adipic acid, glutaric acid and succinic acid.

To this end, the invention provides a novel composition comprising a mixture of diesters of ethylsuccinic acid, methylglutaric acid and optionally adipic acid.

According to another characteristic of the invention, this mixture comprises:
from 70 to 95% by weight of methylglutaric acid diesters
from 5 to 30% by weight of ethylsuccinic acid diesters
from 0 to 10% by weight of adipic acid diesters This composition is obtained starting from a mixture of dinitrile compounds in particular produced and recovered in the process for the manufacture of adiponitrile by double hydrocyanation of butadiene. This process, used on a large scale industrially to produce the great majority of adiponitrile consumed in the world, is described in numerous patents and works.

The reaction for the hydrocyanation of butadiene results predominantly in the formation of linear dinitriles but also in the formation of branched dinitriles, the two main ones of which are methylglutaronitrile and ethylsuccinonitrile.

In the stages of separation and purification of the adiponitrile, the branched dinitrile compounds are separated by distillation and recovered, for example as top fraction in a distillation column.

The invention provides for the conversion of this mixture of branched dinitrile compounds into diesters in order thus to produce a novel solvent.

It can be of interest to eliminate more volatile compounds from the recovered branched dinitrile compounds by a simple distillation for example.

One of the possible processes for the conversion of dinitrile compounds to diesters corresponds to the use of the Pinner reaction, described in particular in French Patent No. 1 488 857. Basically, this process consists in reacting the dinitrile compounds with an alcohol in the presence of a strong inorganic acid, such as sulphuric acid, and in then hydrolysing the products obtained in order to recover the diesters by distillation.

This document also describes a specific embodiment of the process which consists in passing the mixture of dinitrile compounds and the alcohol into a bath of molten salts based on various alkali metal and ammonium sulphates in order to prevent the formation of ammonium sulphate and to recover aqueous ammonia by extraction with steam.

The diesters of the invention can also be obtained by a reaction between the dinitrile compounds, water and an alcohol in the gas phase and in the presence of a solid catalyst. The reaction temperature is advantageously greater than the condensation temperature of the diesters formed. Use may be made, as catalyst, of a solid acid catalyst, such as, for example, a silica gel, a silica/alumina mixture, zeolites, zirconia or supported boric or phosphoric acids. Use may also be made of macroporous aluminas, such as those described in European Patent EP 0 805 801.

The temperature of the reaction is between 200 and 450° C., preferably between 230 and 350° C. The reaction can be carried out under any pressure, advantageously of between 0.1 and 20 bar. At the reactor outlet, the vapours are rapidly cooled to a temperature of less than or equal to 150° C. The ammonia, then the water and the alcohol in excess are separated by distillation from the mixture obtained.

The diesters of the invention can also be obtained by reaction between the dinitrile compounds and an inorganic base, in order to obtain acid salts, then neutralization of these salts by an acid, followed by esterification with an alcohol. Salts of diacids and in particular the ammonium salt of the diacids can be obtained by enzymatic hydrolysis of the nitrile compounds, such as described, for example, in patents EP596812, FR2700777.

Finally, the diesters are purified according to purification processes conventionally used in the technical field of the preparation of organic compounds and in particular by distillation in one or more columns.

According to the invention, the mixture of diesters in accordance with the invention exhibits specific properties different from the properties of the mixture of diesters obtained by esterification of linear carboxylic acids.

More particularly, it exhibits a crystallization temperature of less than −50° C., which makes possible use within a very broad temperature range with a low viscosity of the solvent.

By way of comparison, the solvent resulting from the mixture of linear carboxylic acids has a crystallization temperature of between −20° C. and +20° C., depending on their composition.

The composition of the invention also exhibits a low solubility in water. Equally, the solubility of water in the composition is less than 2.5% by weight at 23° C.

The diesters forming the composition according to the invention are obtained by reaction of an alcohol with the abovementioned dinitrile compounds. Mention may be made, as alcohol which can be used for the manufacture of these compounds, of branched or unbranched and cyclic or acyclic aliphatic alcohols which can comprise an aromatic ring and which can comprise from 1 to 20 carbon atoms.

Mention may be made, as preferred examples, of the following alcohols: methanol, propanol, isopropanol, benzyl alcohol, ethanol, n-butanol, isobutanol, pentanols, cyclohexanol, hexanol, isooctanol or 2-ethylhexanol.

The composition of the invention can be used alone or as a mixture with other solvents or with water in the form of a solution or emulsion. In particular, they can be used as a mixture with the diesters of the linear diacids mentioned above.

These compositions have applications as solvent in numerous fields, such as paints, varnishes and lacquers, the industry for coating surfaces or any other article, such as cables, for example, the ink industry, lubricants for textiles, binders and resins for foundry cores and moulds, cleaning products, cosmetic formulations, for the implementation of certain chemical reactions, in soil and plant treatment compositions and more generally the use, alone or in a formulation, as cleaning, pickling or degreasing solvent in any industrial or domestic activity.

These compositions can also be used as plasticizers for some plastics or as monomers for the manufacture of polymers.

Other advantages or characteristics of the invention will be described in more detail and will be better illustrated in the light of the examples given below purely by way of illustration.

Example 43.26 g of a mixture A of dinitrile compounds are charged with 76.90 g of methanol to a glass reactor with a capacity of 500 ml equipped with a vertical reflux condenser and a stirrer and heated by an oil bath.

The mixture A of dinitrile compounds is composed of:
86.9% by weight of methylglutaronitrile
11.2% by weight of ethylsuccinonitrile
1.9% by weight of adiponitrile.

The remainder to 100% corresponds to the impurities present in this mixture, which are generally not dinitrile compounds.

The dinitrile compounds/methanol mixture is cooled to approximately 1° C. before the addition of 84.22 g of 98% by weight sulphuric acid.

The reaction medium is heated to reflux and is maintained at this temperature for 3 h. The reaction mass is heterogeneous and fluid. After cooling to 60° C., 63 g of water are added. The reaction medium is maintained at 65° C. for 2 hours.

117 g of additional water are then added. The reaction medium becomes two-phase. After removing the excess methanol by evaporation, the two phases are separated by settling and analysed. The organic phase recovered is washed with a saturated aqueous sodium chloride solution with addition of aqueous ammonia in order to obtain a pH in the region of 7.

Washing is carried out a second time with a saturated aqueous sodium chloride solution.

After distilling the washed organic phase, a mixture with the following composition is obtained:

| | |
|---|---|
| Dimethyl 2-methylglutarate | 89% |
| Dimethyl 2-ethylsuccinate | 9% |
| Dimethyl adipate | 1% |
| Various compounds | 1% |

This mixture exhibits the following properties:
Crystallization temperature (the crystallization point was determined by use of the method described in Standard NFT 20-051): less than −50° C.
Solubility with water:
Solubility of water in the composition: 2.2% by weight
Solubility of the composition in water: 2.5% by weight
This value was determined using a container equipped with a stirrer at a temperature of 23° C., either by addition of water to 20 g of diester composition or by addition of the diester composition to 50 g of water, until a cloudy solution was obtained.
Resistance to Hydrolysis:
Acidity is produced by adding 5 g of diester composition to 95 g of water comprising 8 millimol of NaOH. The flask is placed for several days in a chamber heated to 50° C.

The acidity of the medium is measured periodically in order to monitor the fall in the pH.

These tests were carried out with the diester composition of the invention and, by way of comparison, with a diester composition resulting from a mixture of linear diacids sold by Rhodia under the trade name RPDE.

They show that the composition of the invention is more resistant to hydrolysis than the RPDE composition.

Likewise, comparative tests were carried out in order to evaluate the solvating power of the diesters of the invention in comparison with that of the RPDE composition of Rhodia.

These tests were carried out by mixing, in a container, resins commonly employed in the painting field with a predetermined amount of solvent formed of diesters or RPDE.

The results observed are listed in Tables I and II below:

TABLE I

| | RPDE solvent (% by weight) | | | | |
|---|---|---|---|---|---|
| Resins | 10% | 20% | 30% | 40% | 50% |
| Epikote 828 epoxy Sold by Resolution Performance Product | Soluble | soluble (very slight cloudiness after 2 days) | soluble (slight cloudiness after 2 days) | soluble (slight cloudiness after 2 days) | Soluble |
| Tolonate HDT isocyanate Sold by Rhodia | Soluble | Soluble | Soluble | | Soluble |

TABLE I-continued

| Resins | RPDE solvent (% by weight) | | | | |
|---|---|---|---|---|---|
| | 10% | 20% | 30% | 40% | 50% |
| Coporob 2526 alkyd Sold by Novance | Soluble | Soluble | | | Soluble |
| Coporob 335 60 alkyd Sold by Novance | Soluble | Soluble | | | Soluble |
| Macrynal SM516 polyacrylic polyol Sold by Solutia | Soluble | Soluble | | | Soluble |

TABLE II

| Resins | Diesters of the invention (% by weight) | | | | |
|---|---|---|---|---|---|
| | 10% | 20% | 30% | 40% | 50% |
| Epikote 828 epoxy | Soluble | soluble (very slight cloudiness after 2 days) | soluble (slight cloudiness after 2 days) | soluble (slight cloudiness after 2 days) | Soluble |
| Tolonate HDT isocyanate | Soluble | Soluble | Soluble | | Soluble |
| Coporob 2526 alkyd | Soluble | Soluble | | | Soluble |
| Coporob 335 60 alkyd | Soluble | Soluble | | | Soluble |
| Macrynal SM516 polyacrylic polyol | Soluble | Soluble | | | Soluble |

The above tests show that the solvating power of the diesters of the invention is at least equivalent to that of the solvent RPDE.

The invention claimed is:

1. A solvent comprising a mixture, the mixture comprising diesters of ethylsuccinic acid, diesters of methylglutaric acid, and diesters of adipic acid, wherein the concentration by weight of the diesters of methylglutaric acid is 70 to 95%; the concentration of diesters of ethylsuccinic acid by weight is 5 to 30%; and the concentration of diesters of adipic acid by weight is less than or equal to 10%.

2. The solvent as defined by claim 1, wherein the solvent exhibits a crystallization temperature of less than −50° C.

3. The solvent as defined by claim 1, wherein the solubility of water therein is less than or equal to 2.5% by weight at 23° C.

4. A cosolvent medium comprising the solvent as defined by claim 1.

5. A method for solvating a paint, a furnished, or a lacquer, the method comprising contacting said paint, varnish, or lacquer with the composition of claim 1.

6. A composition comprising the solvent of claim 1, wherein the composition is a paint, a varnish, a lacquer, a coating composition, an ink, a lubricant, a binder for foundry cores and moulds, a resin for foundry cores and moulds, a cleaning product, a cosmetic formulation, a soil treatment composition, a plant treatment composition, a cleaner, a pickling composition or a degreaser.

7. The solvent of claim 1, wherein the concentration by weight of the diesters of adipic acid is 1% to 10%.

* * * * *